(12) United States Patent
Stemme et al.

(10) Patent No.: US 7,258,805 B2
(45) Date of Patent: Aug. 21, 2007

(54) MICRO NEEDLES AND METHOD OF MANUFACTURE THEREOF

(76) Inventors: Göran Stemme, Ruddammsvägen 31 B, S-114 21Stockholm (SE); Patrick Griss, Rötelstrasse 126, CH-8057 Zürich (SE)

( * ) Notice: Subject to any disclaimer, the term of this patent is extended or adjusted under 35 U.S.C. 154(b) by 273 days.

(21) Appl. No.: 10/486,541

(22) PCT Filed: Aug. 14, 2002

(86) PCT No.: PCT/SE02/01456

§ 371 (c)(1),
(2), (4) Date: Aug. 11, 2004

(87) PCT Pub. No.: WO03/015860

PCT Pub. Date: Feb. 27, 2003

(65) Prior Publication Data

US 2004/0267205 A1    Dec. 30, 2004

(30) Foreign Application Priority Data

Aug. 14, 2001  (SE)  .................................... 0102736

(51) Int. Cl.
*A61M 5/00*  (2006.01)
(52) U.S. Cl. ............................ 216/2; 216/11; 216/216; 216/56
(58) Field of Classification Search .................... None
See application file for complete search history.

(56) References Cited

U.S. PATENT DOCUMENTS

| 5,676,850 | A | * | 10/1997 | Reed et al. ..................... 216/2 |
| 6,132,755 | A |   | 10/2000 | Eicher et al. |
| 6,334,856 | B1 | * | 1/2002 | Allen et al. .................. 604/191 |
| 6,406,638 | B1 | * | 6/2002 | Stoeber et al. ................. 216/11 |
| 6,558,361 | B1 | * | 5/2003 | Yeshurun ..................... 604/272 |
| 6,743,211 | B1 | * | 6/2004 | Prausnitz et al. ........... 604/239 |
| 6,815,360 | B1 | * | 11/2004 | Canham et al. ............. 438/706 |
| 6,931,277 | B1 | * | 8/2005 | Yuzhakov et al. ............ 604/21 |
| 6,980,855 | B2 | * | 12/2005 | Cho ............................. 604/20 |
| 7,132,054 | B1 | * | 11/2006 | Kravitz et al. ................ 216/11 |
| 2002/0045859 | A1 |   | 4/2002 | Garstein et al. |
| 2004/0054393 | A1 | * | 3/2004 | Stemme et al. ............. 607/149 |
| 2004/0126707 | A1 | * | 7/2004 | Liu et al. ..................... 430/320 |

FOREIGN PATENT DOCUMENTS

| DE | 100 65 168 A1 | 7/2002 |
| FR | 2 535 602 | 5/1984 |
| WO | WO 01/52731 A1 | 7/2001 |
| WO | WO 02/062242 A1 | 8/2002 |

* cited by examiner

*Primary Examiner*—Allan Olsen
(74) *Attorney, Agent, or Firm*—Young & Thompson

(57) ABSTRACT

A micro-needle protrudes from a support member. The needle has a needle body portion, a closed pointed tip portion, and an inner lumen extending through the support member and into the protruding needle. The needle body portion has at least one side opening communicating with the inner lumen. The method of making the needle comprises providing a mask on the front side of an etchable wafer such that the vertical projection of the mask at least partially covers the extension of a hole made in the back side. The mask is isotropically underetched to remove wafer material. An anisotropic etch forms a protruding structure. Optionally a second isotropic etch on the protruding structure exposes the blind hole. Optionally a final anisotropic etch extends the needle without forming side openings.

8 Claims, 14 Drawing Sheets

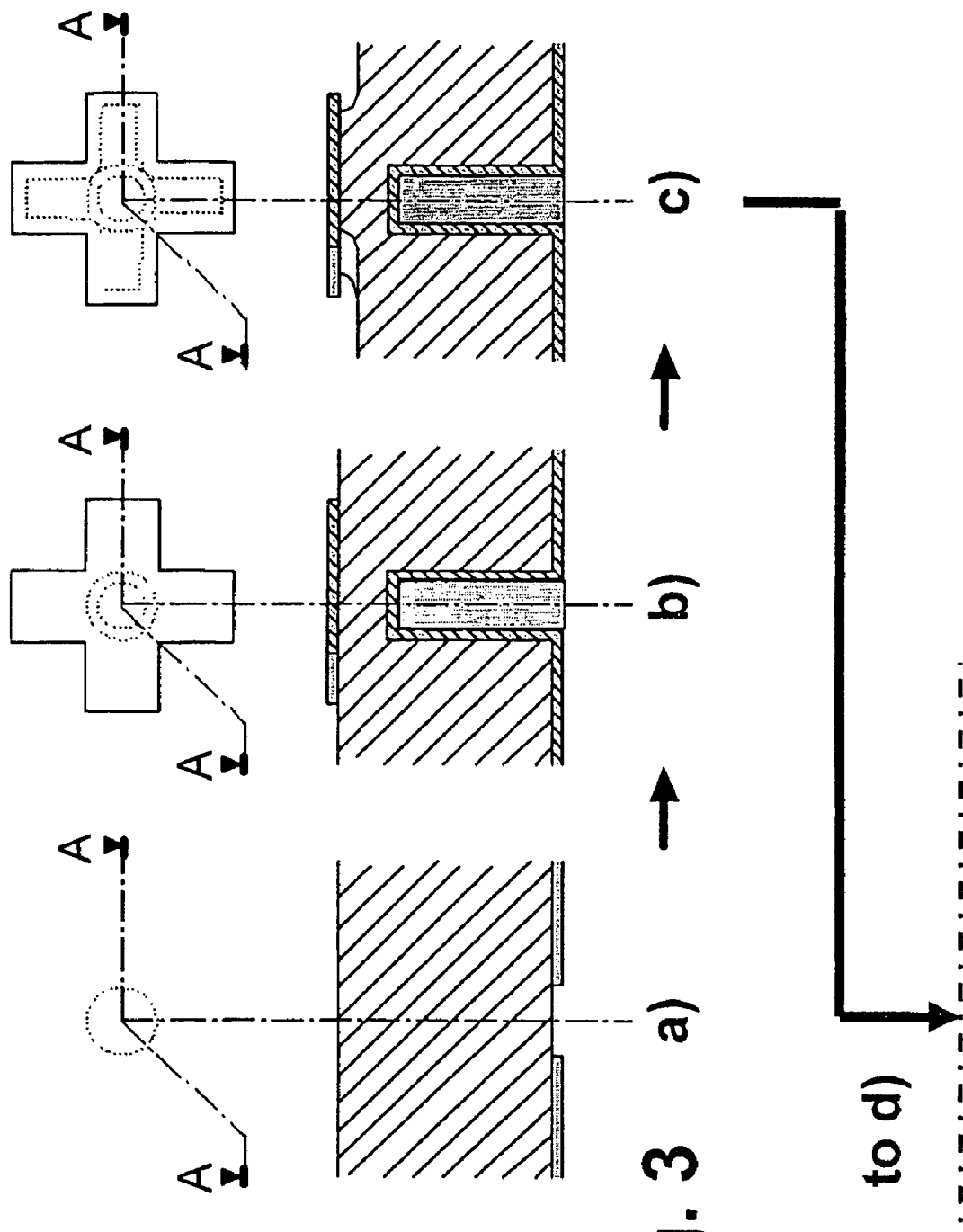

MICRO NEEDLES AND METHOD OF MANUFACTURE THEREOF

The present invention relates to hollow out-of-wafer-plane silicon micro needles having side openings in the shaft. These needles are well suited for transdermal microfluidic applications, e.g. drug- or vaccine delivery

BACKGROUND OF THE INVENTION

The outer most skin layer, i.e. the Stratum Corneum (SC), is perhaps the most versatile biological barrier in the human body. It is an excellent electrical insulator and it prevents the uptake of infectious agents while restricting water loss. The delivery of small amounts of liquids through the SC of humans into the underlying tissue or the sampling of fluids from the underlying tissue is becoming increasingly important in biomedical applications. Microsystem Technology provides means for the fabrication of microscaled liquid transfer needles, i.e. micro needles (micro needle). In the last few years, activity in the micro needle field has been steadily growing. Due to their small dimensions, they can be inserted into the skin painlessly and cause less tissue damage than conventional hypodermic needles. Micro needles have the potential to become the preferred drug delivery device in applications where the transdermal aspect is essential. For example, biotechnology has produced a generation of novel compounds with great therapeutic promise that generally consist of active macromolecules, e.g. proteins. Their oral administration is complicated and the passive diffusion of those compounds across the skin is not a realistic option.

Different hollow out-of-plane micro needle for transdermal applications have been presented before. They are arranged in two dimensional arrays to decrease flow resistance through the device. The array can be achieved with wafer level processing. The openings are at the top of the needle, which increases the risk for clogging. Examples of such needles are disclosed in e.g. U.S. Pat. Nos. 6,132,755 and 6,334,856.

In-plane micro needles have been developed earlier and are characterized by the opening at the shaft of the needle and are less prone to clogging. Such needles are disclosed in e.g. U.S. Pat. Nos. 5,928,207 and 6,375,148. These needles are generally longer than out-of-plane needles. The fabrication of two-dimensional arrays is more difficult to achieve since it cannot be done on wafer level.

Our own group, in collaboration with Datex-Ohmeda (a division of Instrumentarium Corp.), have reported on solid silicon micro needle arrays successfully used for biopotential measurements. See Griss et al in *Journal of Microelectromechanical Systems*, Volume: 10 Issue: 1, March 2001.

The mechanical strength of those micro needle arrays was observed to be surprisingly high, in particular during measurements of the activity of the brain where the arrays were applied on the forehead of test subjects. The mechanical strength of barbed micro needle was also observed when measuring the attachment force of their arrays pressed into different types of materials. Very low failure rate is a requirement for a micromachined micro needle device to be used in commercial applications. In the case of hollow micro needle designed for transdermal liquid transfer, they must be robust enough to penetrate biological tissue and withstand harsh treatment. Coating in-plane single crystalline silicon micro needle with Parylene provides a way to prevent catastrophic failure. This allowed the retraction of micro needle from pierced gelatin membranes, even if the silicon core is fractured. Two dimensional needle arrays are less prone to fracturing when exposed to shear forces during penetration than single needles of the same material and dimensions since the shear stress created by the tissue is distributed over a large amount of micro needle.

SUMMARY OF THE INVENTION

In view of the drawbacks with prior art needles, the object of the present invention was to develop a micromachined structure, and a method for the fabrication thereof, that has the potential to be used in transdermal fluidic applications. The needles should exhibit low flow resistance, high structural strength, large area of drug exposure to the tissue and low risk of clogging. These considerations led to a novel type of out-of-plane micro needle array where the micro needles have openings in the side of the needle rather than at the top. Therefore, when pressed into the tissue, the sharp micro needle tip sections the tissue rather than stamping out a piece of it. The size of the side openings can be controlled through process parameters. The area of drug exposure is increased for a side-opened needle when compared to a tip-opened one, given the same diameter of the liquid channel in the needle.

Thus, the invention provides novel hollow out-of-wafer-plane micro needles having side openings in the shaft rather than having an orifice at the tip, such needles according to the invention being defined in claim 10. This kind of needle structure is well suited for transdermal microfluidic applications, e.g. drug- or vaccine delivery. The deep reactive ion etching (DRIE) process according to the invention allows fabrication of two dimensional, mechanically highly resistant needle arrays offering low resistance to liquid flows and a large exposure area between the fluid and the tissue. The process according to the invention, as defined in claim 1, does not require much wafer handling and only two photolithography steps are required. Using a 3×3 mm² chip in a typical application, e.g. vaccine delivery, a 100 μl volume of aqueous fluid injected in 2 s would cause a pressure drop of less than 2 kPa. The presented needles are approximately 210 μm long.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus not limitative of the present invention, and wherein.

DETAILED DESCRIPTION OF PREFERRED EMBODIMENTS

In the following we present and discuss the wafer level fabrication process for two different types of side-opened micro needle arrays as well as assembly into a package allowing fluidic flow measurements and application on human skin. Subsequently the mechanical stability is studied and the flow-pressure characteristics is measured and discussed.

Experimental

Needle Design and Fabrication

Figure 1:
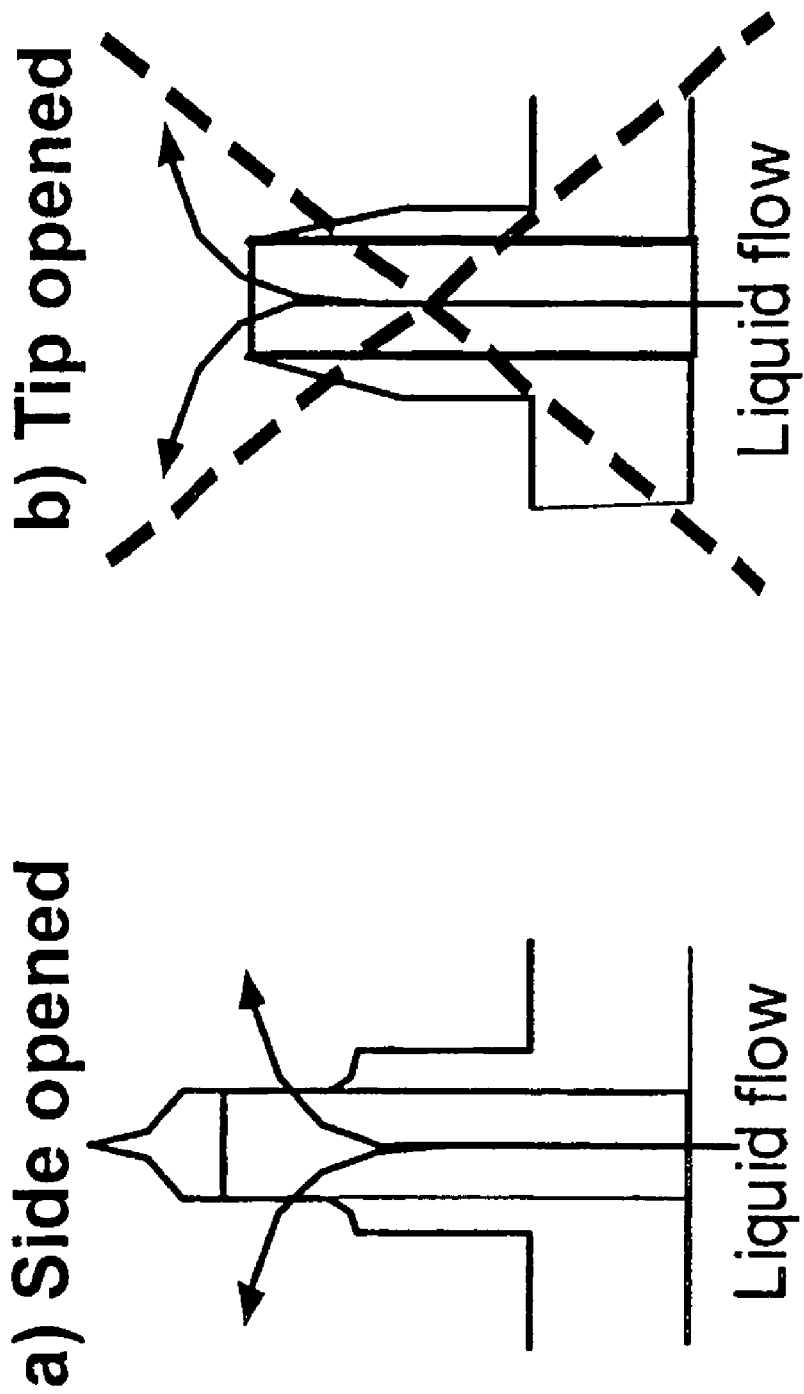
FIG. 1 illustrates the concept of the side-opened out-of-wafer-plane micro needle compared to tip opened ones.
Figure 2:
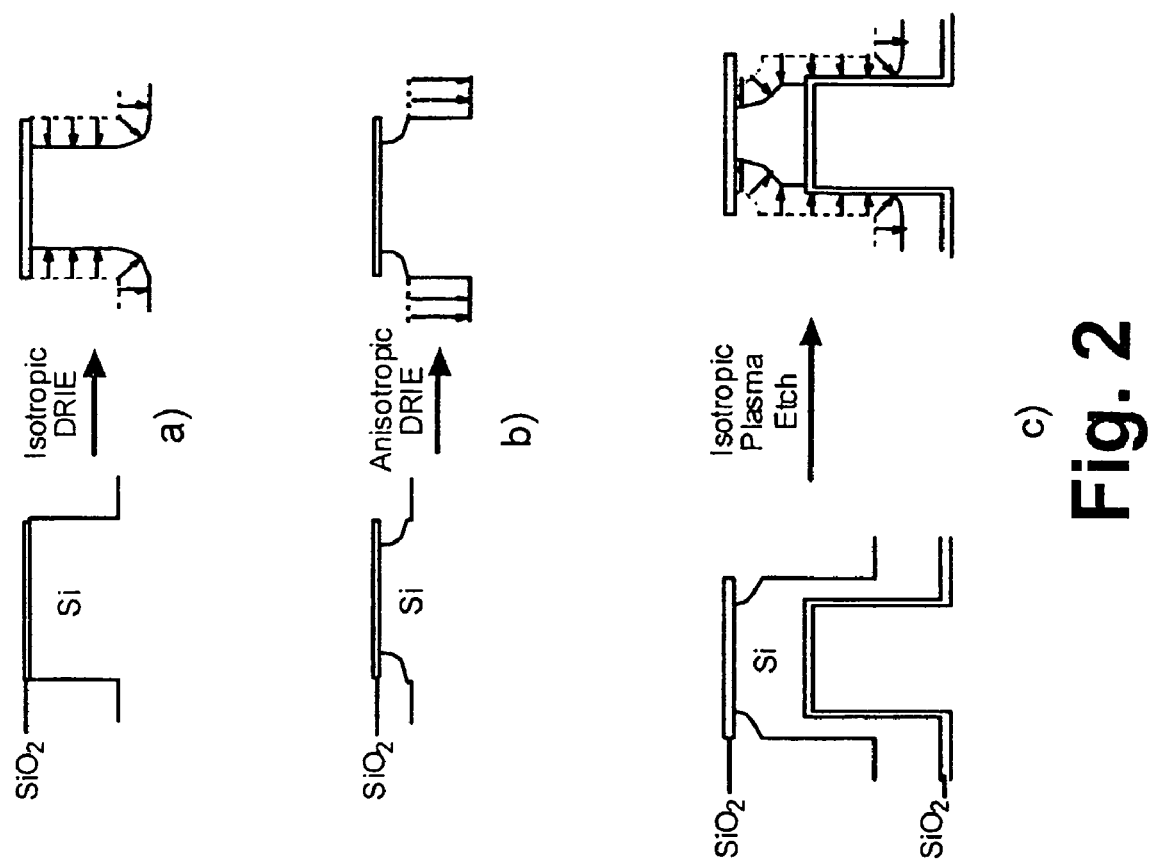
FIG. 2*a* shows how vertical walls of DRIE etched high aspect ratio silicon structures stay vertical during an isotropic plasma etch.
FIG. 2*b* shows that if a silicon dioxide mask is underetched and subsequently anisotropically etched, the resulting section of the structure corresponds to the mask.
FIG. 2*c* illustrates the basic processing principle yielding side openings in high aspect ratio structures (using DRIE technology)

The fabrication of side-opened micro needle is based on the triple DRIE (Deep Reactive Ion Etching) process (see the article by Griss et al mentioned above) shown earlier by our group where it was observed that in this process vertical walls of DRIE etched high aspect ratio silicon structures stay vertical during an isotropic plasma etch, as shown in FIG. 2a). Further, it was observed that if a silicon dioxide mask is underetched and subsequently anisotropically etched, the resulting cross-section of the structure corresponds to the mask, see FIG. 2b). Combining these observations with a vertical high aspect ratio hole from the back side, a DRIE based process for the fabrication of side-opened out-of-plane micro needle was established. A simplified artistic drawing of the process principle is shown in FIG. 2c).

Figure 3:
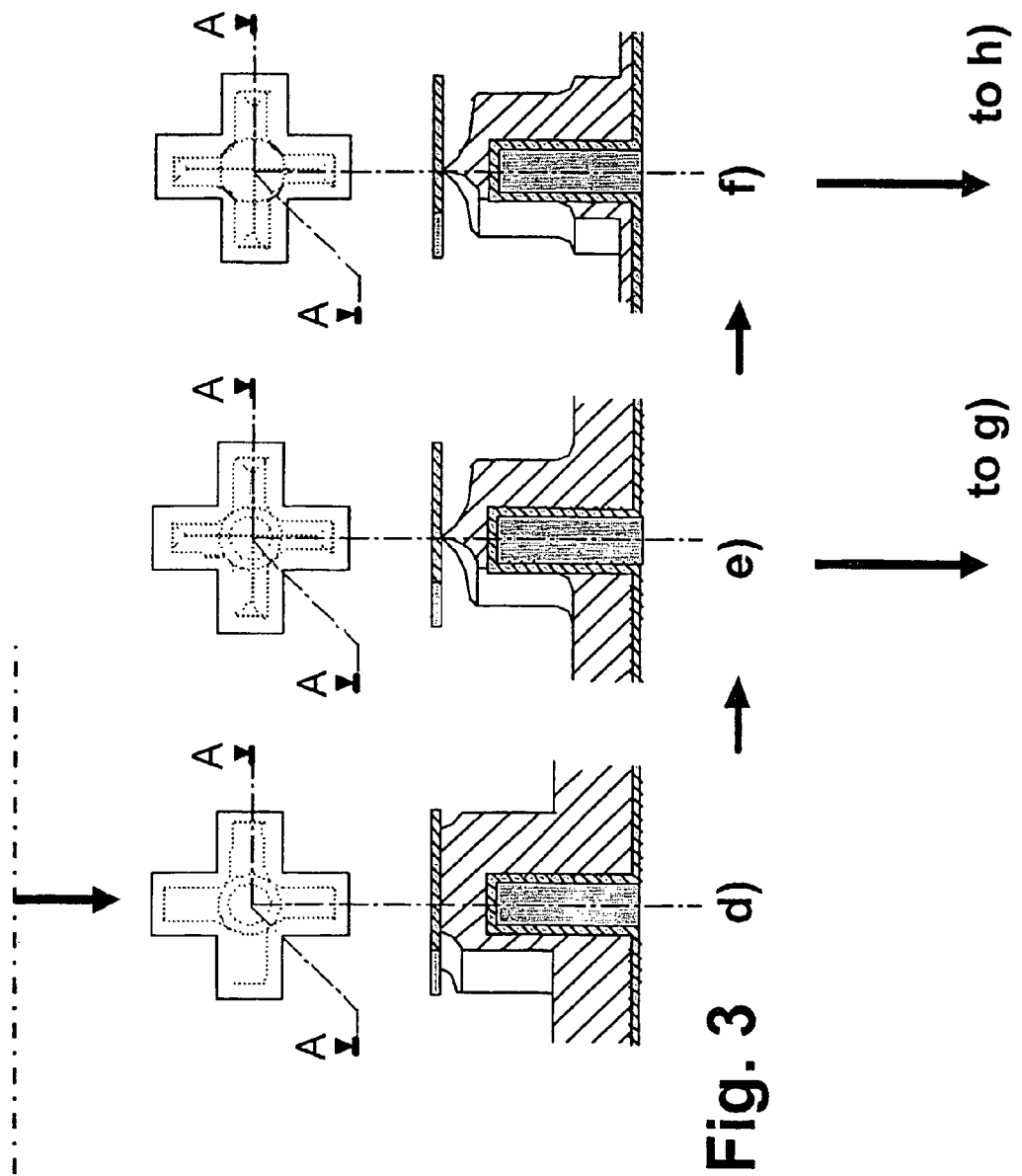
FIG. 3*a-h* shows process flow showing a top view and a cut through the needle along the A-A line. Refer to the text for details.
Figure 3:
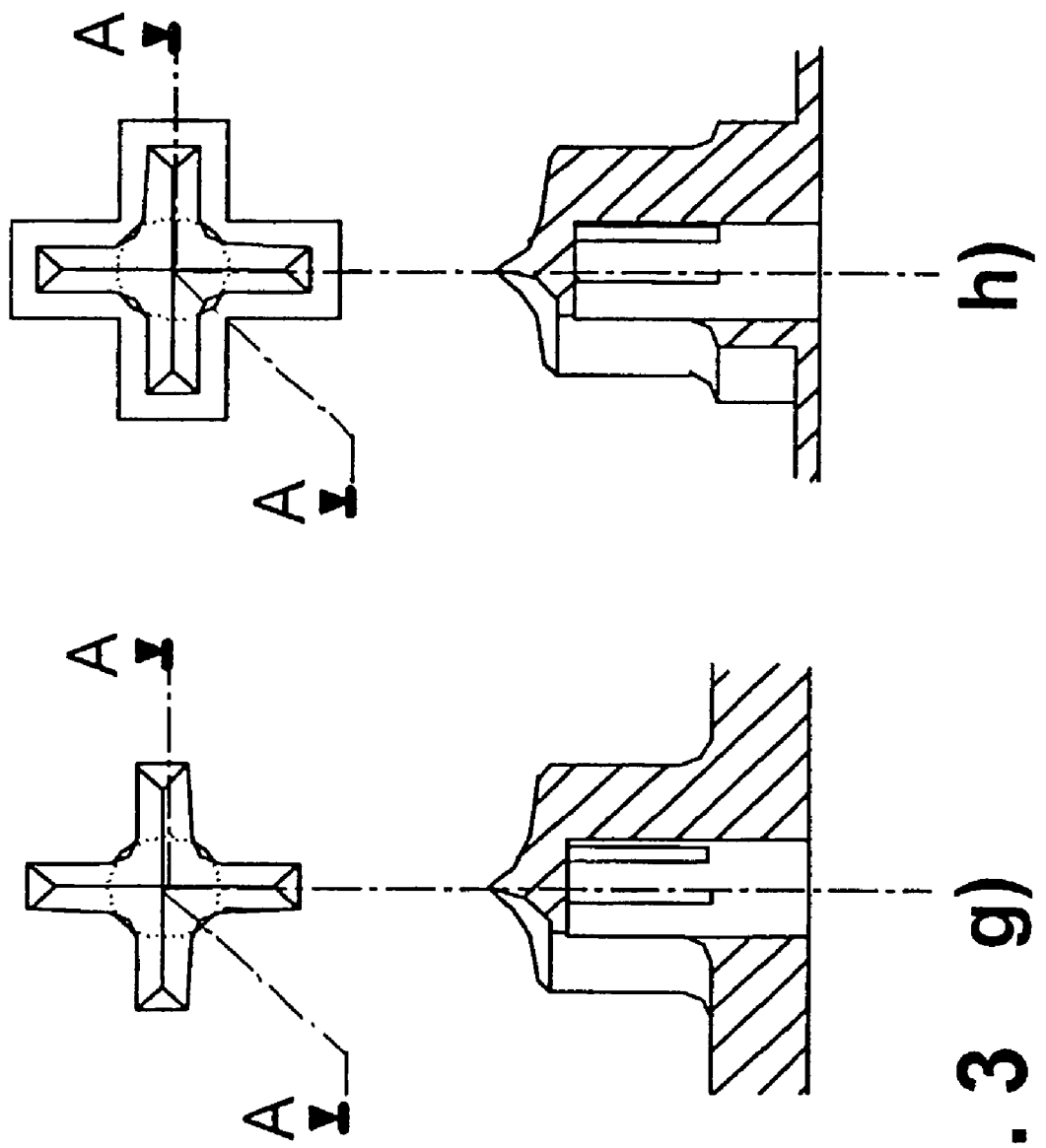

The detailed process flow yielding side-opened micro needle is depicted in FIG. 3. A circular (or any other suitable cylindrical shape) high aspect ratio hole is etched into the back side of the wafer using a silicon dioxide ($SiO_2$) mask in an inductively coupled plasma etcher (ICP) (FIGS. 3a and 3b). Aspect ratio can be The anisotropic etching is based on the Bosch process. The hole serves as a liquid channel connecting the back side of the chip to the front side. After wet oxidation to cover the surface with a thin $SiO_2$ membrane, wet lithography is use to provided a $SiO_2$ cross-shaped mask, aligned to the hole on the front side of the wafer. The diameter of the hole can be, but must not necessarily be smaller than the diagonal dimension of the cross (FIG. 3b). A first isotropic ICP step underetches the $SiO_2$ front mask (FIG. 3c) and is followed by an anisotropic ICP step, which creates a cross-shaped out-of-plane structure without side openings (FIG. 3d). The subsequent isotropic etch decreases the cross sectional area of the structure without altering the angle of the sidewalls, thus creating side openings in the walls that are still closed by a thin $SiO_2$ membrane (FIG. 3e). This etch also sharpens the four pillars of the cross-shaped structure, each pillar having a knife like edge at the top. This step is stopped before the mask is completely underetched at the center. A complete underetch of the mask would destroy the structure since the mask would fall off and probably stick to the sidewall. If side-openings that start at the base of the needle are desired, no additional plasma etch is required. If it is desired that the micro needle has a part where there are no side slits, another anisotropic plasma etch can be performed, which will result in a side hole placed above the needle base. The top mask can be removed by a final wet oxidation followed by a $SiO_2$ HF-strip (FIG. 3g or 3h). The oxidation growth and removal also sharpens the tip apex of the needle. Process steps c to e or f, respectively, are executed in one load of the ICP machine, thus the total process is uncomplicated and does not require much wafer handling. Only two photolithography steps are required to yield a relatively complex three dimensional microstructure.

A generalized definition of the process according to the invention is a method of manufacturing micro-needles protruding from a support body, said needles comprising a body portion, a closed pointed tip portion, and an inner lumen extending through said support body and into said protruding needle, said body portion having side openings communicating with said inner lumen said method comprising the following steps: providing a wafer comprised of an etchable material and having a front side and a back side; making a blind hole in said wafer from its back side; providing a mask on the front side of the wafer such that the vertical projection of said mask at least partially covers the extension of said hole; performing a first isotropic etch under said mask to remove wafer material; anisotropically etching the wafer to form a protruding structure; performing a second isotropic etch on said protruding structure to expose the blind hole; and optionally performing a final anisotropic etch to provide to extend the needle without forming side openings; wherein the position and extension of the mask relative the position and dimension of the hole is such that said side openings form during said second isotropic etch.

Preferably said mask and said hole have the same general geometric shape, but wherein said mask is larger than the cross section of the hole, and wherein the center points of the hole and mask, respectively, are displaced relative to each other.

In one embodiment said mask is larger than the cross section of the hole, and wherein the shapes of the mask and hole, respectively, are different from each other.

In another embodiment mask is larger than the hole, and the center points of the hole and mask, respectively, coincide. Alternatively, said mask overlaps the hole in at least one region. Preferably said blind hole is made by etching.

Packaging/Assembly

Figure 4:
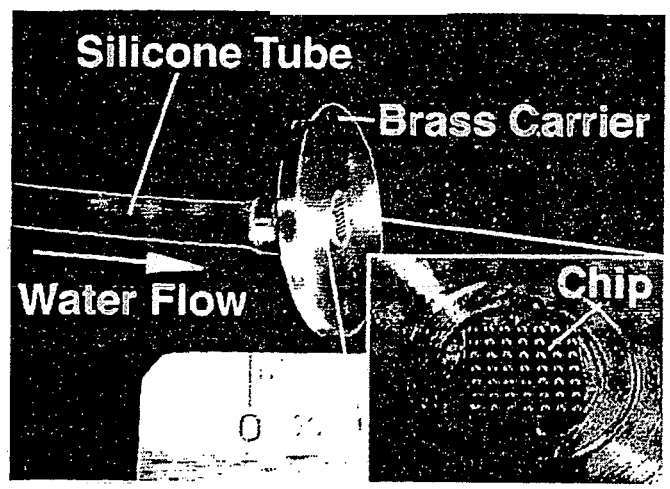
FIG. 4 is a photograph of the assembly used for flow-pressure measurements.

The measurement of the flow resistance requires assembly of the chip containing a side opened micro needle array onto a carrier which allows a connection to fluid tubing, as shown in FIG. 4. The carrier is made of brass and was manufactured using conventional machining methods. The 3×3 mm² chip is fixed to the carrier by means of ultraviolet light curing epoxy (Epotek OG 198). The square geometry of the chip and the circular geometry of the through hole of the carrier results in the blockage of some micro needle at the chip corner. Twenty-one micro needle are not blocked and contribute to the flow through the device.

Figure 5A:
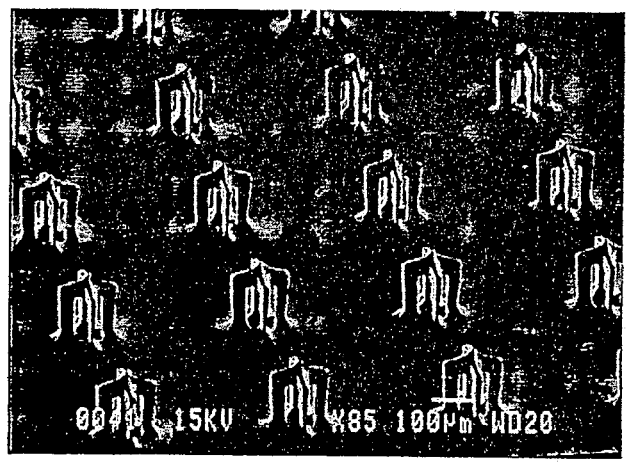
FIG. 5a-b are SEM images of side-opened micro needles, the hole beginning at the base of the needle. The length of the structure is 210 μm.
Figure 5B:
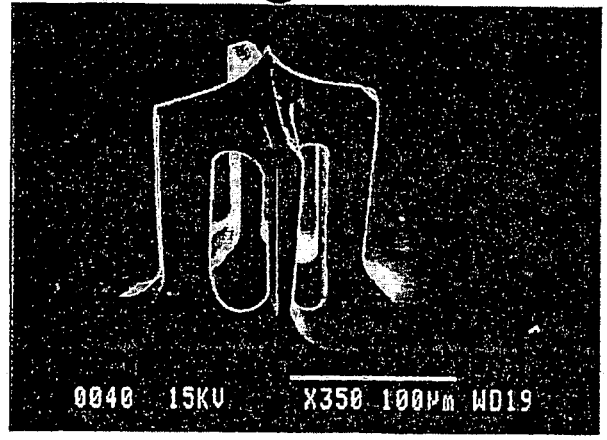
Figure 6A:
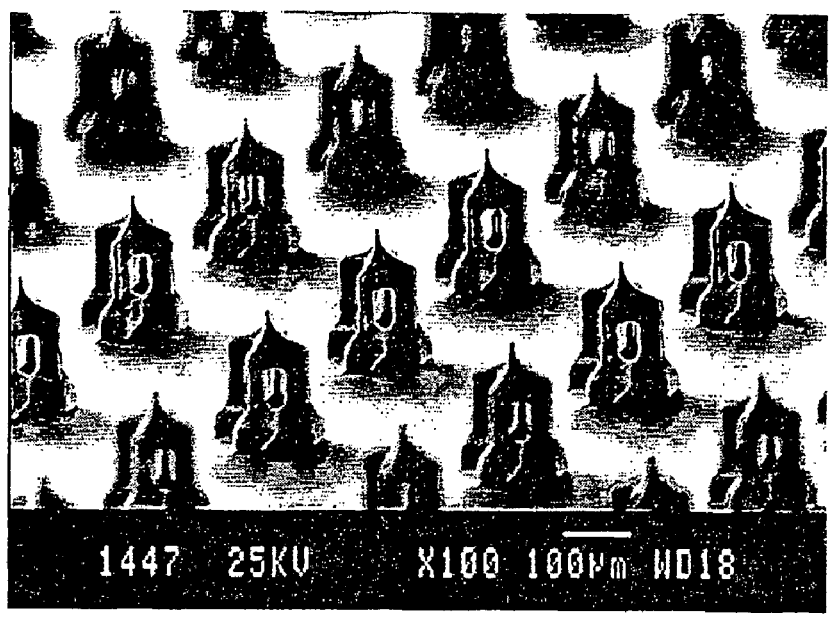
FIG. 6a-b are SEM images of side-opened micro needles, the hole beginning approximately 50 μm above the base of the needle. The length of the structure is 210 μm.
Figure 6B:
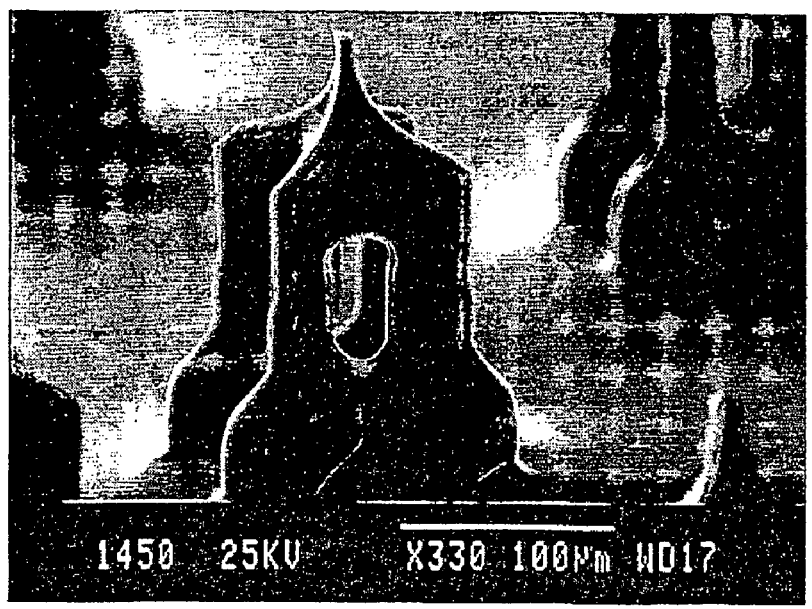
Figure 7:
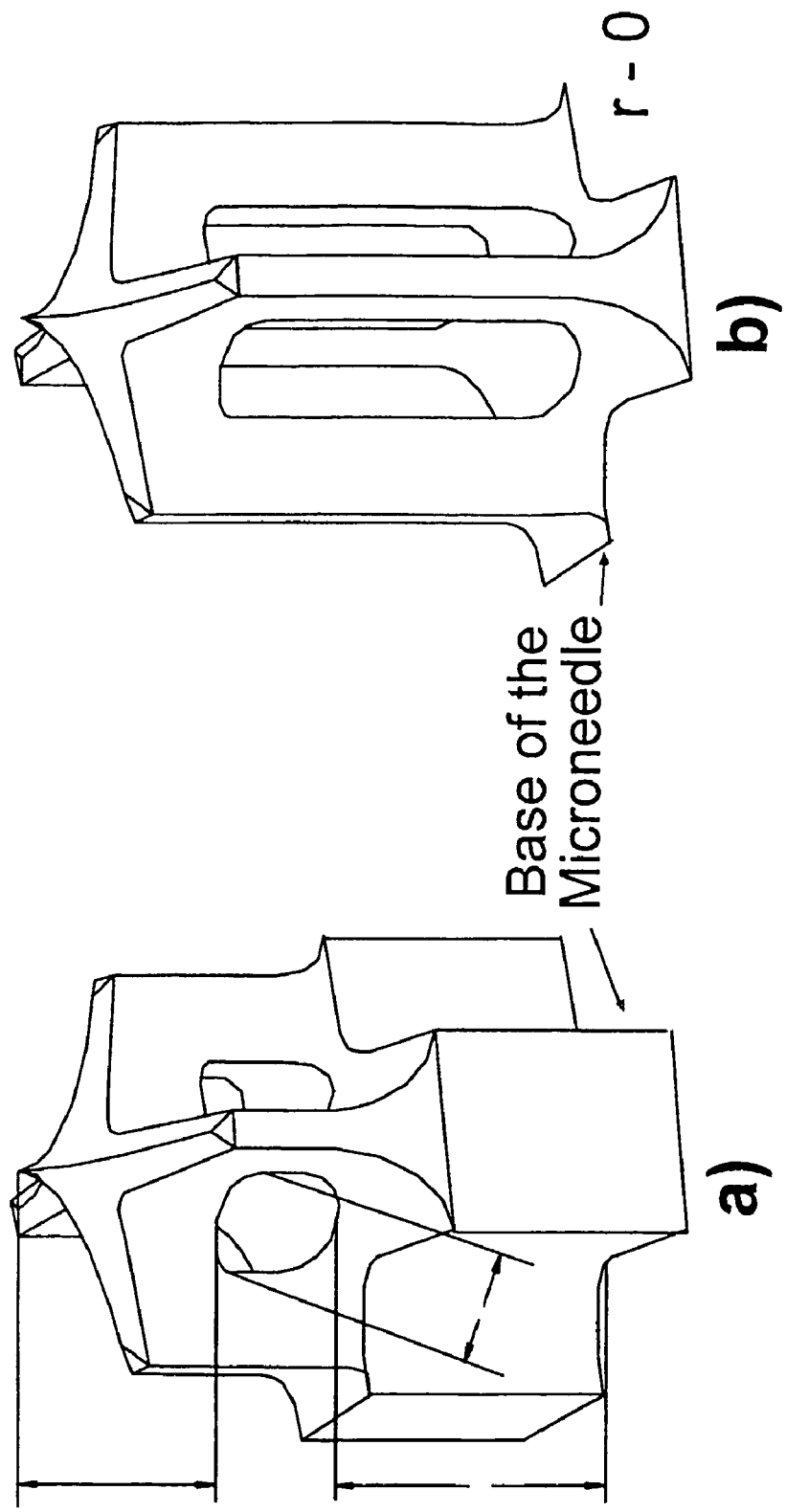
FIG. 7 is a drawing of the micro needles presented in this work. The position of the side opening is defined by process parameters. a) For a given hole and needle mask, the width of the side opening t as well as the position of the side opening (i.e. distance s from the needle tip and distance r above the base) are defined by process parameters. b) if it is desired to start the side opening at the base of the needle, r can be chosen to be zero.
Figure 8:
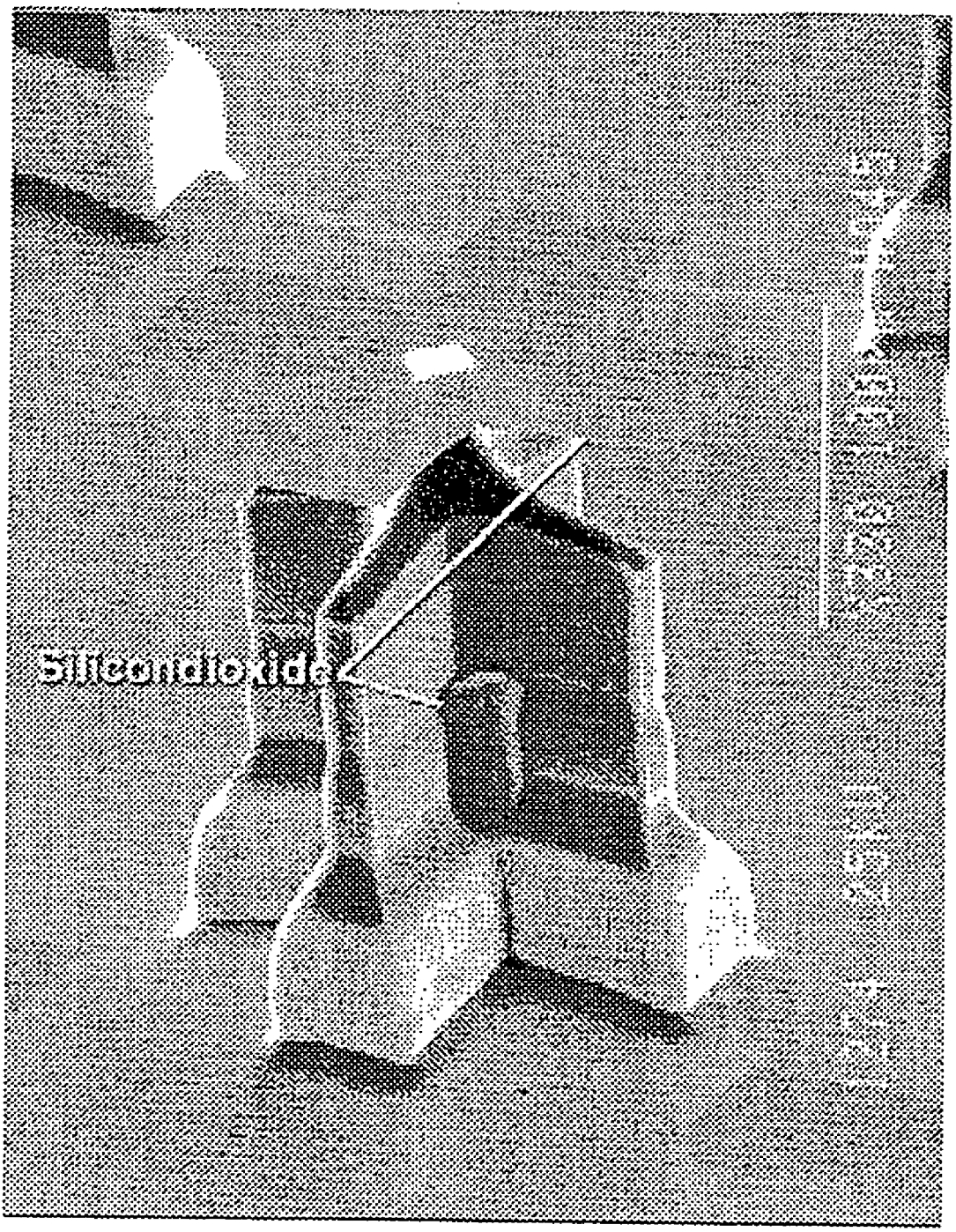
FIG. 8 is a SEM photograph of a side-opened micro needle before the removal of the silicon dioxide front side mask. Where the side opening is located, silicon dioxide is visible and not removed yet.

FIGS. 5 and 6 depict scanning electron microscope (SEM) images of two types of side-opened silicon micro needle. In FIG. 5, the side opening extends from the base of the needle, close to the base/support surface, whereas in FIG. 6 the micro needle has a side opening that extends from a point above the surrounding base/support surface, i.e. the opening starts above the needle base. This feature can be important to prevent leakage of the liquid when the micro needle is inserted into the skin. Both needle types can be achieved with the same mask. As shown in FIG. 7, for a given mask, the width t of the side opening as well as the position of the side opening (i.e. distance s from the needle tip and distance r above the base) are defined by process parameters. This allows for great freedom of design and enables the fabrication of micro needle optimized for a specific application. FIG. 8 depicts a side-opened micro needle before mask removal and sharpening of the apex. A membrane consisting of $SiO_2$ still covers the side opening.

Now the embodiment of FIGS. 7*a*) and *b*) will be described in closer detail.

As already described the micro needle comprises a protruding structure extending vertically from a support surface, said protruding structure having been created by etching procedures. The embodiment in FIG. 7*a*) is generally cross shaped, i.e. it has four wings extending in different directions at right angles. Near the support or base surface (not shown in FIG. 7*a*)) the cross shaped structure is relatively thick, because it has not been exposed to an isotropic plasma etc. In the upper part of the cross shaped structure each of the wings have been exposed to such an isotropic plasma edge, rendering them thinner and wedge like, each having a sharp edge facing upwards. The edges of said wings merge into a pointed tip. The tip and the sharp edges cooperate to provide a structure having excellent penetrating capability, as evidenced by the test on Al foil, shown in FIG. 10.

The side openings are formed by virtue of the fact that the interior cavity (central hole or lumen) of the needle will be reached by the isotropic etch front at certain points before it reaches other points. Namely, in the corners formed by the wings the etch front will encounter the interior cavity long before this would happen at the wings themselves. Thus, the openings will begin to form exactly in the "nook" where the wings meet. As will be evident for the skilled man, the dimensions and location of the openings can be controlled entirely by etch parameters, such as rate, time etc. The thicker bottom portion of the embodiment of FIG. 7*a*) is formed by exposing the structure to an anisotropic etch after the openings have been formed.

In FIG. 7*b*) another embodiment of the micro needle is shown. This embodiment is based on the same mask configuration as the embodiment of FIG. 7*a*), but has a different opening dimension, i.e. the openings have a larger longitudinal extension. This has been accomplished by exposing the structure to a prolonged isotropic etch for the generation of the openings, and refraining from a final anisotropic etch, which would have created a thicker bottom portion like in FIG. 7*a*).

The mask work needed for the embodiments of FIGS. 7*a*) and b) is a cross shaped needle mask and a circular mask for making the hole.

Figure 11:
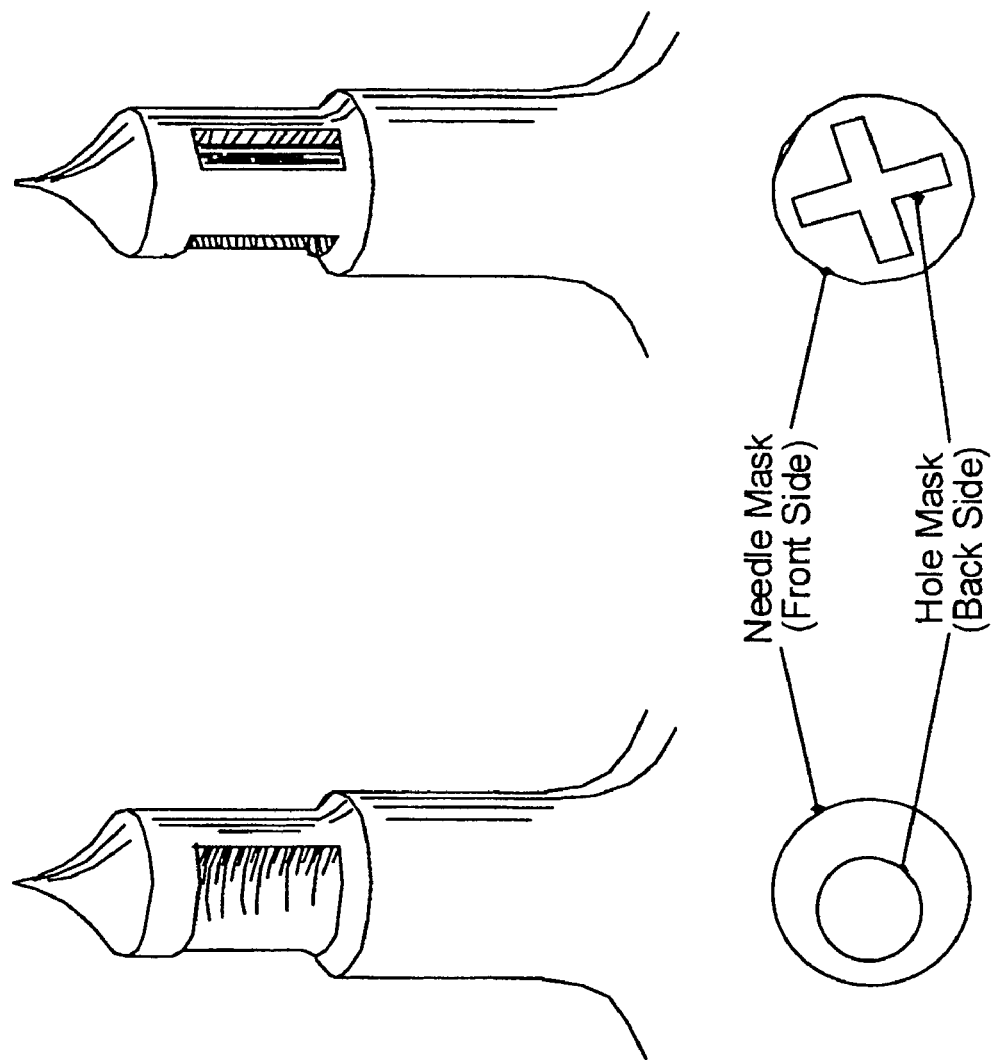
FIG. 11 is a drawing of two side-opened micro neeldes that can be manufactured using the presented process. a) has one single side opening and b) has four side openings. The primary difference between these two micro needles is the hole mask which defines the channel in the micro needle.
Figure 12:
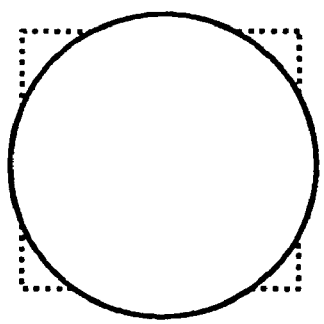
FIG. 12 is a schematic illustration of different mask/hole configurations.
Figure 12:
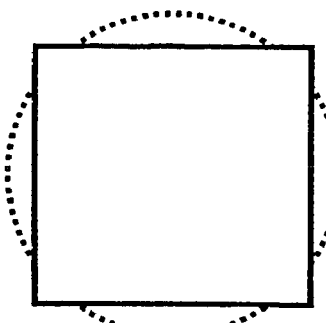
Figure 12:
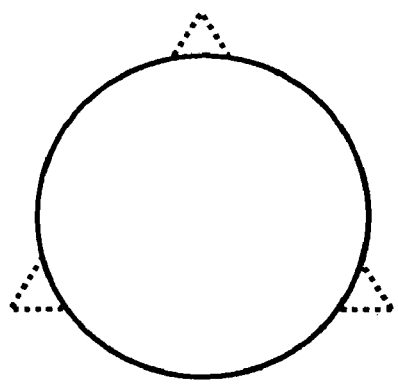
Figure 12:
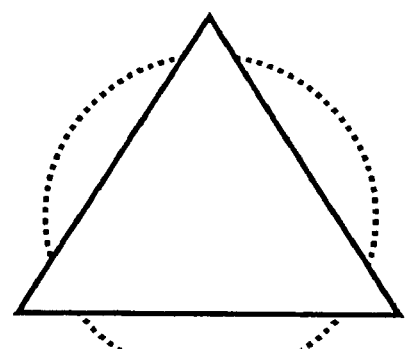
Figure 12:
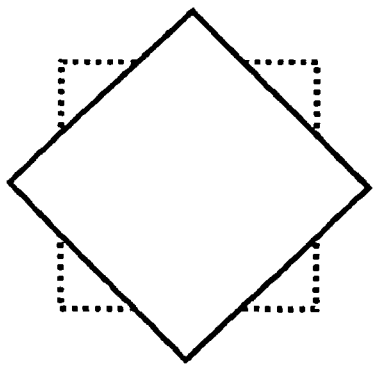
Figure 12:
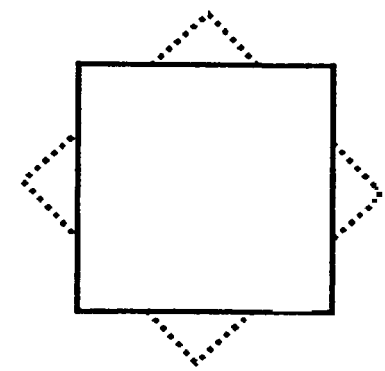
Figure 13:
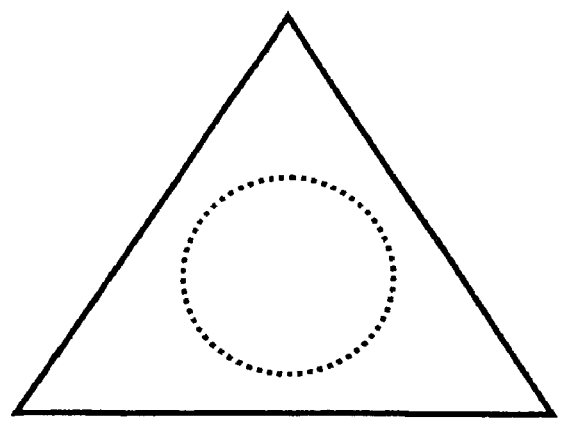
FIG. 13 is a schematic illustration of alternative mask/hole configurations.
Figure 13:
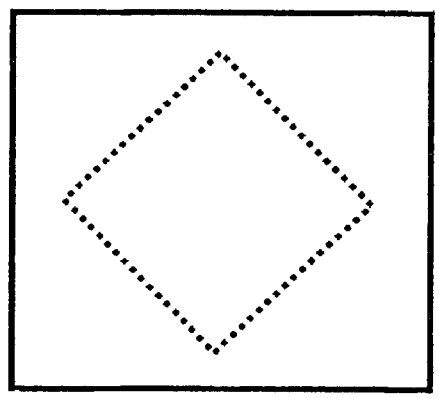
Figure 13:
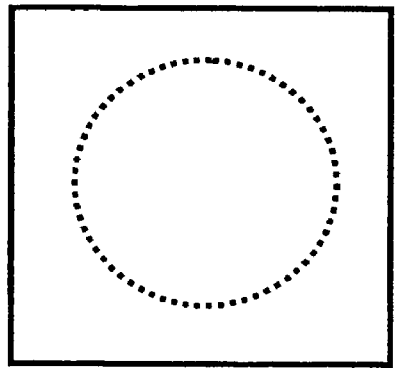

However, several other designs of out-of-plane side-opened micro needle can be imagined. Using a circular needle mask and a cross shaped hole mask, a circular needle with four side holes result as depicted in FIG. 11*b*). Two eccentric circular masks will result in a circular needle featuring one single side opening, as exemplified in FIG. 11*a*). FIGS. 12 and 13 show other combinations of mask and hole configuration as a non-exhaustive exemplification. In FIGS. 12 and 13 the mask is shown as the geometric shape covering the underlying shape, representing the hole, which is represented by dotted lines. Numerous other geometries are possible and are all within the scope of the appended claims. Such variations can be implement without further inventive work after having read and understood the present disclosure.

In a general manner of definition a micro-needle according to the invention protrudes from a support member. The needle comprises a needle body portion, a closed pointed tip portion, and an inner lumen extending through said support member and into said protruding needle. The needle body portion has at least one side opening communicating with said inner lumen. Preferably said side openings extend from a point below said pointed tip portion and towards said support body. Alternatively, the side openings have an extension from a point below said pointed tip portion and to a point above said support member. In a further embodiment said side openings have an extension from a point below said pointed tip portion and down to said support member.

In an at present preferred embodiment of the invention a micro-needle has a general shape of cross exhibiting a plurality of wings, and wherein said side openings are located in the corners of the cross where said wings connect to each other.

In a variation the inner lumen is eccentric relative to said needle body portion. The body portion and said inner lumen both can have the same general geometric shape, but in such a case the cross section of the lumen is smaller than the cross section of the body portion. Said geometric shape can be any of a circle, a rectangle, a triangle, or a polygon, or any other suitable shape that fulfills the purpose of the invention.

In an application of the invention there is provided a device for transdermal transport of liquids across the skin of a patient, comprising an array of micro-needles according to the invention provided on a support member. A liquid storage container is connectable to said micro-needle array, and a pump is provided for feeding said liquid from said storage container to said micro-needle array, for e.g. administration of vaccine. The device is also suitable for sampling liquid through the skin. In such cases the pump is adapted to provide a suction of liquid samples, such as blood through the skin of a patient.

A further way of defining the micro needles of the invention is that the envelope surface (exterior surface) of the needle structure will intersect the envelope surface of the inner lumen within the needle structure in at least one defined region.

Figure 9:
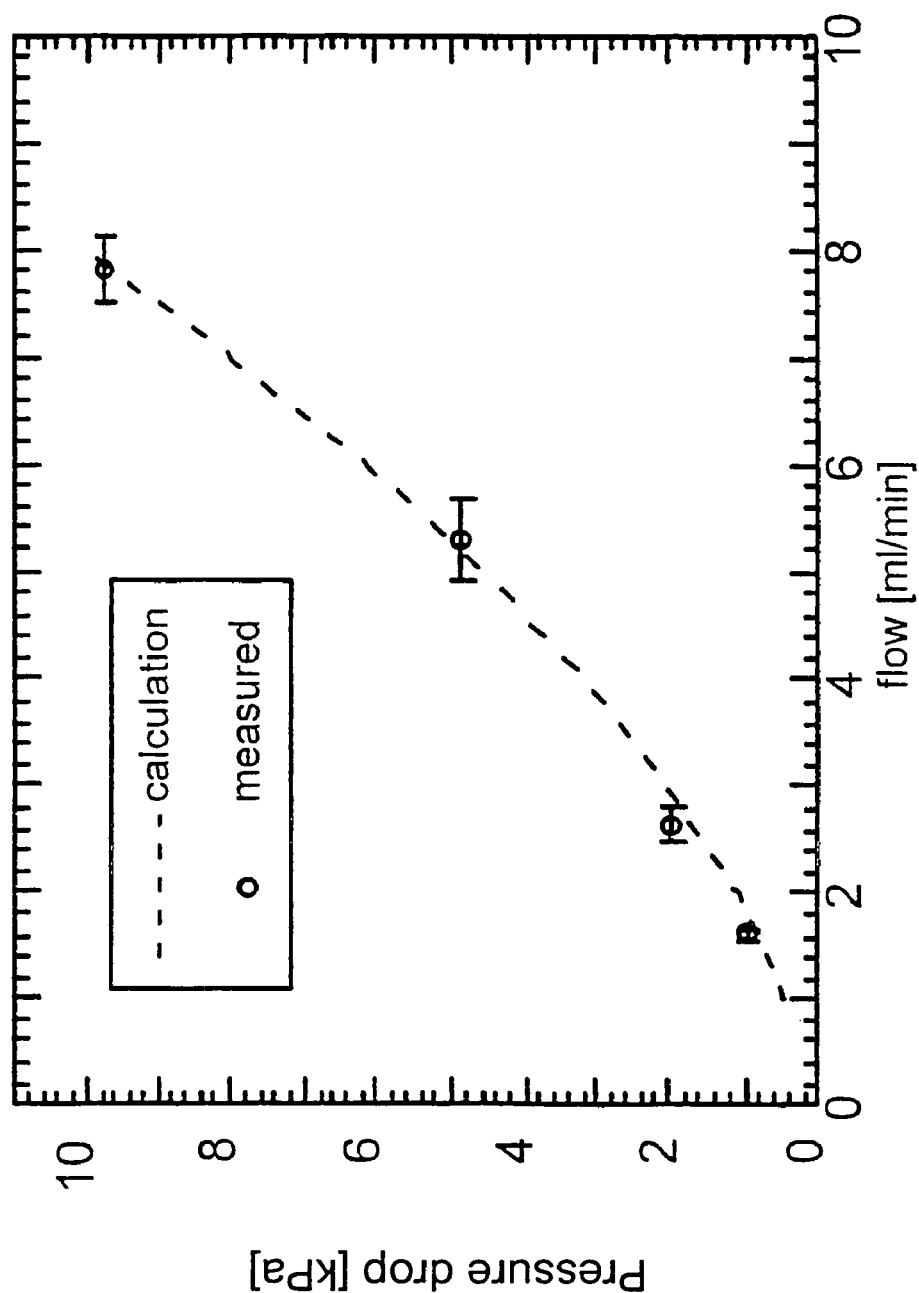
FIG. 9 is a graph showing measurement and calculation of the pressure drop over the chip caused by water flow.

For the purpose of this application, the expression "envelope surface" will be taken to mean a surface that encloses a structure, disregarding any irregularities such as openings therein. Thus the envelope surface of the final needle structure of the embodiment of FIG. 7*a*) is that surface that exactly encloses a cross shaped structure that does not exhibit any openings. Similarly the envelope surface of the inner lumen of the final needle structure of the embodiment of FIG. 7*a*) is that surface that corresponds to and defines the original cylindrical cavity in the needle before Gravimetric flow measurements resulted in the pressure-flow characteristics as shown in FIG. 9. The depicted characteristics are those of a micro needle array (21 needles) and not of a single needle. Theoretical calculations of the flow characteristics are shown in the same Fig. and take into account the viscous shear force of the Poiseuille flow inside a circular tube and the inertia effects [17, 3]. The total pressure drop Δp across the channel is the sum of the pressure drop $\Delta p_R$ due to laminar friction (i.e. Poiseuille) and the pressure drop $\Delta p_B$ required to accelerate the liquid. For a tubular liquid channel this is calculated according to [17]:

$$\Delta p = \Delta p_R + \Delta p_B = \frac{8\eta L}{\pi R^4}\Phi + C_B \frac{\rho}{\pi^2 R^4}\Phi^2$$

where η is the viscosity of the liquid, Φ the flow generating the pressure drop Δp, ρ the density of the liquid, R is the radius of the channel and L the length of the channel. $C_B$ is a numerical factor and in this case it is 1.2.

In a typical transdermal application, e.g. vaccine delivery, a 100 μl volume of aqueous fluid injected through a chip containing 21 side-opened micro needle in 2s would cause a pressure drop of less than 2 kPa. The flow resistance can further be decreased by increasing the number of micro needle (i.e. the number of micro needle per area unit). Since an anisotropic etch mainly defines the length of the micro needle, very high density can be achieved since the mask is only slightly larger than the resulting micro needle. Therefore, the maximum needle density, that is allowed by the inherent capability of the skin of being permeated, can be achieved without being restricted by technology.

If aqueous liquid is presented to the back side of the chip without applying a pressure difference between the front side and the back side, the liquid is sucked into the channels in the chip base by capillary forces. The liquid meniscus is stopped at the side openings without wetting the front side. A pressure of approximately 1 kPa was measured to break through this barrier.

Figure 10:
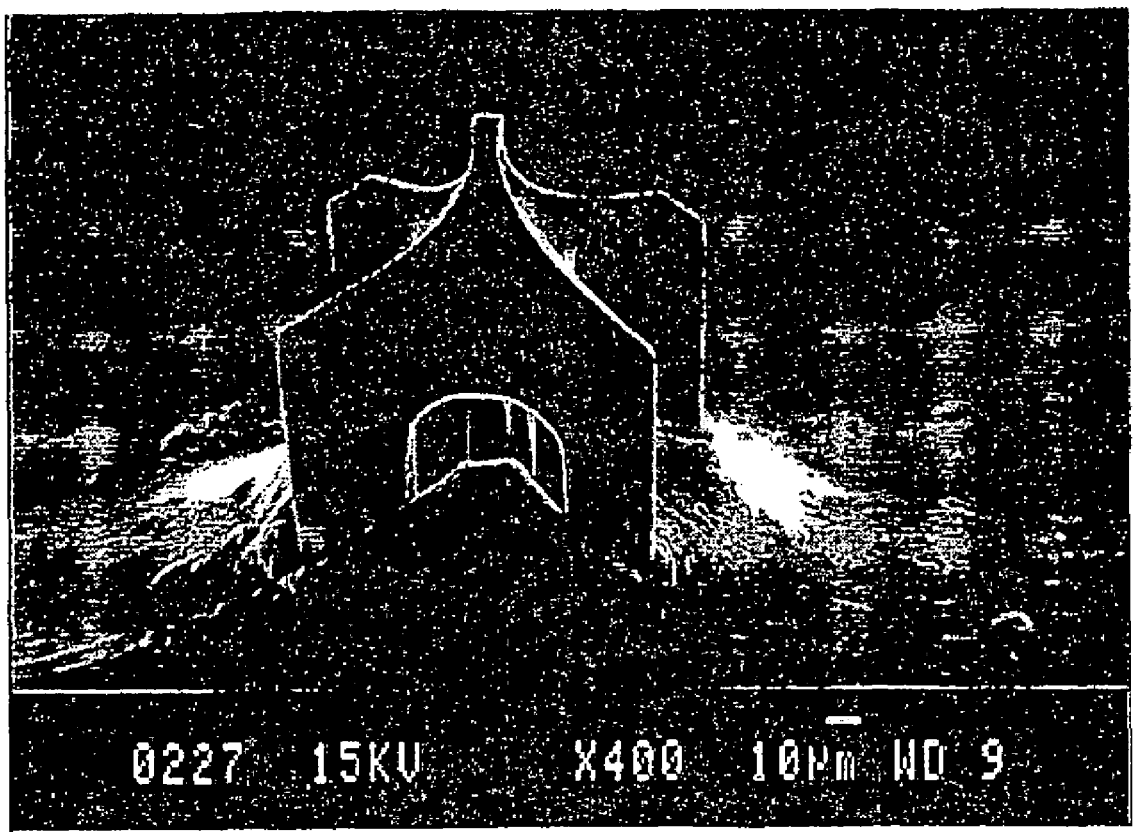
FIG. 10 shows the penetration of a 10 μm thick aluminium foil by side-opened micro needles. Note that no damage can be observed on at the needle.

FIG. 10 exemplifies the mechanical stability of the obtained micro needles. A 10 μm thick aluminium foil is penetrated by a micro needle having side openings without breaking. In this figure, the side openings start at the base of the micro needle. This type is theoretically more fragile than those where the side openings start above the needle base. Note that the shown structure was not oxidized long enough to yield a sharp apex, in contrast to the one shown in FIG. 5. It was observed that assembled side-opened micro needle can be pressed into human skin and removed from human skin repeatedly without breaking.

Thus, the present invention provides a new technology for the fabrication of arrays of hollow out-of-plane micro needles that have openings in the shaft rather than at the tip apex. For a given and specific mask design, the size and position of the side openings are defined by process parameters, and thus not by the specific mask design itself.

Such needles allow new opportunities for transdermal liquid transfer. The measured flow resistance of a packaged side-opened needle array is low (and can further be decreased if needed by increasing the needle density). The mechanical strength of the needle arrays is high. Subsequent penetration and removal to and from the skin does not result in the destruction of the needles. The mechanical strength is also demonstrated by the ability to pierce aluminium. Potentially, the shown structures are less prone to clogging than tip-opened counterparts and the large size of the side openings allows a large area of liquid exposure to the skin.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method of manufacturing a micro-needle protruding from a support body, said needle comprising a body portion, a closed pointed tip portion, and an inner lumen extending through said support body and into said protruding needle, said body portion having side openings communicating with said inner lumen, the method comprising the following steps:

providing a wafer comprised of an etchable material and having a front side and a back side;

making a blind hole in said wafer from its back side;

providing a mask on the front side of the wafer such that the vertical projection of said mask at least partially covers the extension of said hole;

performing a first isotropic etch under said mask to remove wafer material;

anisotropically etching the wafer to form a protruding structure; and optionally performing a second isotropic etch on said protruding structure to expose the blind hole;

wherein the position and extension of the mask relative the position and dimension of the hole is such that said side openings form during either said anisotropic etch or said second isotropic etch.

2. The method as claimed in claim 1, comprising performing a final anisotropic etch to extend the needle without forming side openings.

3. The method as claimed in claim 1, wherein said mask and said hole have the same general geometric shape, but wherein said mask is larger than the cross section of the hole, and wherein the center points of the hole and mask, respectively, are displaced relative to each other.

4. The method as claimed in claim 1, wherein said mask overlaps the hole in at least one region.

5. The method as claimed in claim 1, wherein said blind hole is made by etching.

6. The method in claim 1, wherein the shapes of the mask and the cross section of the hole, respectively, are any of a circle, a rectangle, a triangle, or a polygon.

7. The method as claimed in claim 1, wherein said mask is larger than the cross section of the hole, and wherein the shapes of the mask and hole, respectively, are different from each other.

8. The method as claimed in claim 7, wherein said mask is larger than the hole, and wherein the center points of the hole and mask, respectively, coincide.

* * * * *